United States Patent [19]

Coleman et al.

[11] Patent Number: 4,932,414

[45] Date of Patent: Jun. 12, 1990

[54] SYSTEM OF THERAPEUTIC ULTRASOUND AND REAL-TIME ULTRASONIC SCANNING

[75] Inventors: D. Jackson Coleman, Haworth; Frederic L. Lizzi, Tenafly, both of N.J.

[73] Assignees: Cornell Research Foundation, Inc., Ithaca; Riverside Research Institute, New York, both of N.Y.

[21] Appl. No.: 115,729

[22] Filed: Nov. 2, 1987

[51] Int. Cl.$^5$ .............................................. A61B 8/00
[52] U.S. Cl. .......................... 128/660.09; 128/660.03; 128/660.07; 128/916
[58] Field of Search ............. 128/660, 661, 663, 24 A, 128/660.01, 916, 660.09, 660.03, 660.07; 73/625

[56] References Cited

U.S. PATENT DOCUMENTS

| | | | |
|---|---|---|---|
| Re. 30,397 | 9/1980 | King | 128/916 |
| 4,271,706 | 6/1981 | Ledley | 128/660 |
| 4,275,597 | 6/1985 | Quedens et al. | 128/660 |
| 4,294,119 | 10/1981 | Soldner | 128/660 |
| 4,341,120 | 7/1982 | Anderson | 128/916 |
| 4,343,301 | 8/1982 | Indech | 128/24 A |
| 4,570,488 | 2/1986 | Wiwa et al. | 128/916 |
| 4,620,546 | 11/1986 | Aida et al. | 128/660 |
| 4,637,256 | 1/1987 | Sugiyama et al. | 128/660 |
| 4,658,828 | 4/1987 | Dory | 128/660 |
| 4,674,057 | 6/1987 | Caughman et al. | 73/625 |
| 4,699,007 | 10/1987 | Kawashima et al. | 73/625 |
| 4,771,787 | 9/1988 | Wurster et al. | 128/24 A |
| 4,798,210 | 1/1989 | Ledley | 128/660.01 |

OTHER PUBLICATIONS

Ultrasound 3-D Techniques, *Biomedical Ultrasonics*, by P. N. T. Wells, Academic Press, 1977, pp. 248-252.
An "Add-On" Modification for Linear Array Real Time Ultrasound Scanners to Produce 3 Dimensional Displays. Conference: Ultrasonics International 1977, Brighton, England, Jun. 28-30, 1977.
Ultrasonic Three-Dimensional Imaging and Volume from a Series of Arbitrary Sector Scans, by Brinkley et al., Ultrasound in Med. & Biol., vol. 4, pp. 317-327, (1978).

*Primary Examiner*—Francis Jaworski
*Assistant Examiner*—George Manuel
*Attorney, Agent, or Firm*—Sughrue, Mion, Zinn, Macpeak & Seas

[57] ABSTRACT

A system is described for obtaining in real-time cross-sectional and 3-dimensional images of a body under study using ultrasonic energy. A piezoelectric transducer is positioned to emit ultrasonic energy and receive echo pulses. The transducer is electronically swept or physically rotated to produce a series of sectored scan planes which are separated by a known angular distance. The echo pulses are processed to produce an ultrasonic image in pseudo 3-dimensional display. By using data from one scan plane, processed as a B-scan image, cross-sectional data can be obtained. Such is combined in a display with an overlay to visually portray the object and positioning information or comparative data. The system is combined with a computer for data analysis and a therapeutic transducer for treatment.

44 Claims, 6 Drawing Sheets

SYSTEM OF THERAPEUTIC ULTRASOUND AND REAL-TIME ULTRASONIC SCANNING

This invention was made in the course of work under a grant from the National Institutes of Health.

BACKGROUND OF THE INVENTION

This invention relates to a system of ultrasonic diagnosis and therapy. In particular, this invention relates to the use of ultrasonics for providing in real-time, cross-sectional and 3-D images of an organ for diagnosis and utilizing the same system to treat disorders by non-invasive means. The invention combines two components, a real-time ultrasonic piezoelectric diagnosis unit and a high intensity, focussed therapeutic ultrasonic sub-system.

Ultrasonic transducers used for non invasive therapeutic applications are known in the art. Such ultrasonic transducer assemblies generally comprise a housing and a transducer mounted within the housing for radiating a converging beam of acoustic energy in response to an applied electrical signal. The beam of acoustic energy converges to a focal point which is usually the therapeutic point of application. Such devices have found utilization in the treatment of disorders of the eye or other organs by non-invasive means.

The applications of ultrasound in the field of ophthalmology is discussed, for example, in Coleman et al. "Therapeutic Ultrasound in the Production of Ocular Lesions", Amer. J. of Ophthal., Vol. 86, No. 2, pp. 185-192, 1978 and Coleman, et al. "Applications of Therapeutic Ultrasound in Ophthalmology" Progress in Medical Ultrasound, pp. 263-270 (1981). The use of a paraxial diagnostic transducer is disclosed to allow manual positioning of the therapeutic focus within the targeted zone. The position of the therapeutic focus within the targeted zone is monitored by observation of a diagnostic B-scan or A-scan display. Once positioned, the therapeutic transducer is actuated for the desired application of ultrasound for example the production of lesions.

U.S. Pat. No. 3,735,755 discloses a complete ultrasonic system employing a transducer assembly used by the operator for both display and treatment. The complicated system disclosed therein is cumbersome and does not provide the level of data needed to perform difficult procedures in real-time in a simple clinical setting.

B-scan diagnosis devices and transducers are also discussed in U.S. Pat. Nos. 4,141,347 and 4,237,901.

Ultrasonic techniques have also been employed successfully in lithotropsy. In systems using acoustic shock wave generation the transducer may be employed together with an ultrasonic positioning unit. The extent of therapeutic action is determined by subsequent X-ray. Alternatively, a separate ultrasonic scanner may be employed in a paraxial arrangement for positioning.

Reference is made to U.S. Pat. No. 4,617,931 which relates to a transducer for producing shock waves and an auxiliary ultrasonic transducer disposed paraxially and mechanically swept. Use of the piezoelectric transducer itself for positioning is disclosed in Ziegler et al, "Extracorporeal Piezoelectric Lithotropsy". A commercial system employing B-scan and a lithotropic transducer is the Piezolith 2200 manufactured by Richard Wolf GMBH and described in Riedlinger et al, "Die Zertrummerung von Hierensteinen durch piezoelektrisch erzengte Hochonergie-Schallpulse", urologe [A] (1986) 25:188-192. Reference is also made DE 27 22 252 Al and a Dornier system technical description entitled "Entwicklung eines Verfahrens zur beruhrungsfreien Zerkleinerung von Hierensteinen durch StoBwellen" (1976).

Reference is made to U.S. Pat. No. 4,484,569, entitled "Ultrasonic Diagnostic and Therapeutic Transducer Assembly and Method for Using", commonly assigned, which is expressly incorporated herein by reference. The system described therein allows the use of the single transducer assembly to generate acoustic energy for purposes of either diagnosis by generating A-scan images or, to use ultrasonic beams for non-invasive treatment.

Using the technology of the '569 patent, with the patient properly prepared, the transducer assembly that houses the therapeutic and diagnostic transducers is first used for diagnostic purposes to allow displays for the practitioner so that the organ under scrutiny may be explored. Once this diagnostic phase is completed, ultrasonic energy from the same transducer assembly may be used to perform non-invasive treatment of the organ. The power to the therapeutic transducer produces a burst of high energy acoustic radiation applied to the site requiring treatment. Following the application of a therapeutic beam, the initial diagnostic transducer may be used to provide A-scan and ultrasonic echoes to determine changes in tissue characteristics. The process is then repeated on an iterative basis until the treatment has been completed.

The '569 patent also allows for visual positioning of the therapy beam by the use of a light beam radiated through the transducer by means of a fiber optic conduit.

While this system offers important advantages in the treatment of tissue disorders, especially those of the eye, a need exists to provide viewing and data collection of diagnostic information for 2- and 3-dimensional positioning, i.e., aiming and for information concurrent with therapeutic application of ultrasound. Concurrent monitoring would allow the practitioner to apply intense ultrasound to tissue on a real-time basis, and judge the condition of the insonified tissue during irradiation. This in turn would permit a determination of whether further treatments are called for and the precise location for such treatment.

It is therefore an object of this invention to provide for a new and improved ultrasonic system which allows for the concurrent diagnosis and therapeutic application of ultrasonic waves to tissue.

An important object of this invention is to provide a system of three dimensional ultrasonic echo image generation.

Yet another object of this invention is to provide a system of real-time monitoring of ultrasound therapy to assess the dynamic response within tissue during and immediately after insonification.

A further object of this invention is to provide for an ultrasonic system wherein viewing and data collection of diagnostic information occur concurrently with therapeutic applications.

A still further object of this invention is to provide a system of visual image display depicting tissue regions that are likely to be modified by selecting specific exposure conditions such as time, intensity, beam profile, frequency and the like.

SUMMARY OF THE INVENTION

In accordance with this invention, a system is provided that integrates a rapid scan, real-time diagnostic ultrasonic system with a therapeutic ultrasonic system. The real-time diagnostic portion of the system provides three-dimensional and/or cross-sectional images of the tissue under scrutiny in real-time. Preferably, in the case of the eye the diagnostic transducer is a broad band B-mode device with a 10 MHz center frequency housed in an assembly that is physically attached to the therapeutic transducer assembly. The diagnostic transducer may be a single element or an array of elements in one or two dimensions. The therapeutic transducer assembly contains a high-intensity piezoelectric transducer and a coupling cone filled with degassed, distilled water held in place with a thin, acoustically transparent rubber membrane. The therapeutic transducer assembly may also contain a central diagnostic transducer for axial positioning and a central fiber optic system whose projected light beam specifies the central axis of the therapeutic beam. This subcomponent is described in U.S. Pat. No. 4,484,569, previously incorporated herein by reference.

In order to obtain 3-dimensional images, the real-time diagnostic transducer is rotated to obtain sequential scan planes. This rotation can take place by either physically rotating the real-time transducer assembly or electrically scanning with a transducer array. In the case of physically rotating the position of the transducer assembly would be determined by a shaft encoder or by using a stepper motor to move the transducer in a known manner. If the real-time transducer comprises an array, scanning can occur by sequential excitation of the array elements to obtain a series of output pulses indicative of data from each scan plane. In this mode of implementation the array is fixed in a known orientation so that a predetermined angular separation exists between scan planes. In both cases, the signals can be appropriately gated to select an area for data acquisition within each scan plane.

In a preferred embodiment of the system, the diagnostic transducer assembly is attached to the cone of the therapeutic transducer assembly. This attachment allows the practitioner to adjust the rotation, angulation and position of the scanning diagnostic transducer and to lock the two transducer assemblies in place, so that the position and orientation of the therapeutic beam can be fully specified within the set of B-scan planes.

This invention will be described in greater detail by reference to the accompanying drawings and the description of the preferred embodiment which follows.

DESCRIPTION OF THE PREFERRED EMBODIMENT

Figure 1:
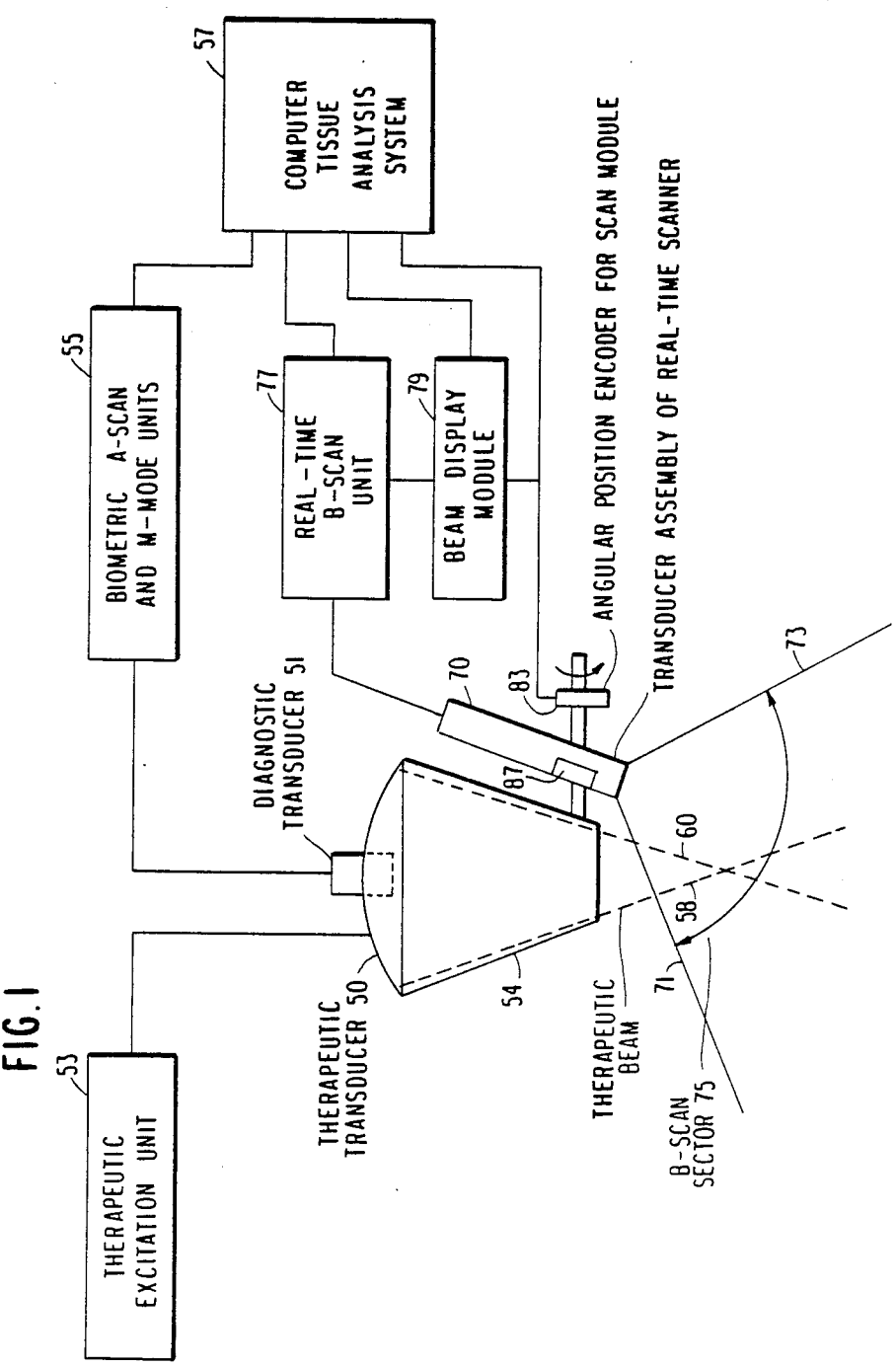
FIG. 1 is a block diagram of the system of this invention for carrying out concurrent, real-time ultrasonic diagnosis and therapeutic application.

Referring now to FIG. 1, a block diagram of the system in accordance with this invention is depicted.

The block diagram of FIG. 1 depicts a complete proposed clinical system which employs both a therapeutic transducer and a real-time B-scan unit to obtain pseudo 3 dimensional displays of reflective structures in a human organ or, of other material objects. The therapeutic transducer 50 and its associated electronics are described and discussed in detail in U.S. Pat. No. 4,484,569 which is expressly incorporated herein by reference. The therapeutic transducer 50 also includes a fixed diagnostic transducer 51 and is attached to a coupling cone 54. The therapeutic transducer 50 is actuated by a therapeutic excitation unit 53 and the diagnostic transducer 51 is coupled to a biometric A-scan and M-mode unit 55. A computerized tissue analysis system is employed for the purpose of diagnosing tissues prior to application of the therapeutic beam and to closely monitor subtle changes which may be induced by therapy. That computerized tissue analysis system is discussed in detail in copending patent application Ser. No. 641,015 filed on Aug. 15, 1984, and entitled A Method for Enhancement of Ultrasonic Image Data.

The diagnostic transducer 51 may have a fiber optic source used for precise lateral positioning of the therapeutic transducer as disclosed in the '569 patent.

An important aspect of this invention is the use of a B-scan unit coupled to the therapeutic transducer coupling cone 54 but either mechanically rotated or electrically swept to obtain data for 3-dimensional presentation. The scan outline 71, 73 defines the angular limits of B-scan sector 75. As illustrated in FIG. 1, one such sector defines a scan plane. Electronics for the B-scan transducer are contained in a real-time B-scan unit 77 which provides an output to a beam display module 79. The beam outline for each scan plane is stored in a digital memory contained in the beam display module 79. FIG. 1 also illustrates that the output from the real-time B-scan unit 77 and the beam display module 79 are used to provide inputs to the computer tissue analysis system 57.

Figure 2:
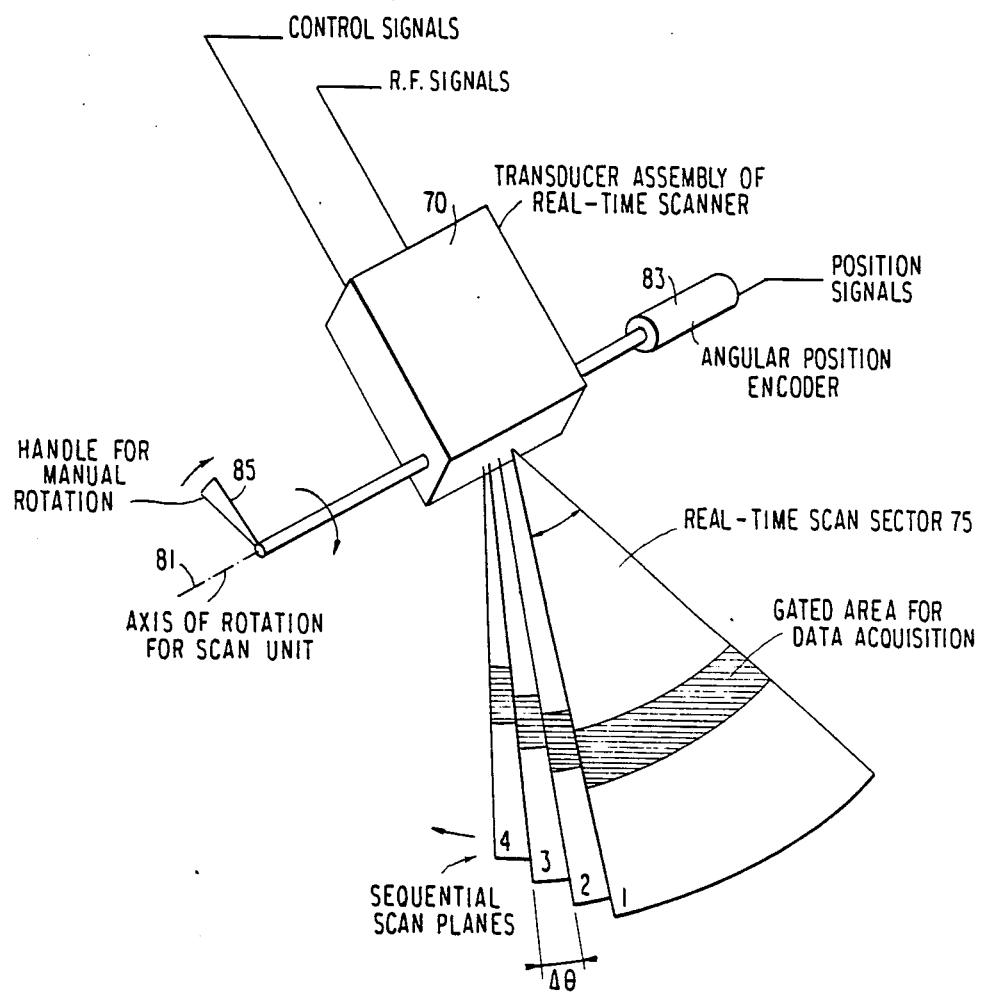
FIG. 2 is a schematic drawing illustrating the scanning mechanisms for serial plane examinations.

Referring now to FIGS. 1 and 2, the scheme for obtaining ultrasonic echo data from a sequence of scan planes with known orientations is depicted. The B-scan unit is schematically depicted in FIG. 2 in a housing 70. As illustrated therein, ultrasonic echo data from a sequence of scan planes with a known orientation describes a 3 dimensional position of reflective structures in a human organ or a material object. If those images from each plane are displayed in rapid succession, in real-time, the impression of 3 dimensional geometry is obtained. The data may also be entered into a digital image processing system such as an ADAGE 3000 to produce pseudo three dimensional displays.

As illustrated in FIGS. 1 and 2 this system preferably incorporates a real-time B-scan diagnostic transducer assembly. In the case of ophthalmic use, a typical assembly would have a small piezoelectric transducer to send ultrasonic pulses toward the eye and receive echo pulses returned by structures in the eye. In each scan plane 75, the transducer would be scanned in a sector format to obtain 2-dimensional cross-sectional data. In many instruments the transducer would be rotated by means of a small motor housed in the assembly 70. The motor, 87, pivots the transducer about an axis which is perpendicular to the scan plane defined by element 75. FIG. 2 illustrates schematically the electrical connections required to excite the transducer, drive the motor and convey rf voltage signals generated by the transducer in response to each ultrasonic echo pulse. Such are coupled to the real-time B-scan unit 77.

The above paragraph describes operations within a single scan plane. To obtain 3-dimensional data a plurality of scan planes are examined by rotating the real-time transducer assembly about an axis 81 perpendicular to one or the other each scan plane (illustrated by arrow in FIG. 2).

The orientation of the entire transducer assembly 70 at each instant in time may be determined by using a small stepper motor (not illustrated). In such a system, control of the transducer motion would be effectuated by using appropriately configured voltage pulses so that each pulse would cause a known angular shift in transducer assembly position. Alternatively, a position encoder such as a potentiometer illustrated in FIGS. 1 and 2 as element 83 can be used to sense transducer orientation and generate appropriate output voltages as position signals to the beam display module 79 and the computer 57. Instead of the motor, a handle 85 may be used to achieve manual rotation of the transducer assembly 70.

A preferred technique of determining the angular position of the transducer is to use an optical encoder. Such an encoder utilizes a grid of clear and opaque radial lines which alternate in a sector pattern rotating with the shaft. The encoder employs a light source on one side of the encoder and a light detector on the other side. As the light beam traverses the grid, the detector generates a voltage output changing as the light beam is interrupted by the opaque grid lines. Since the angular separation of the radial grid lines is known, the occurrence of each voltage pulse is indicative of an angular increment of movement of the shaft. Such optical shaft encoders are well known. Another technique could be the use of a position encoder such as a sine-cosine potentiometer.

As illustrated in FIGS. 1 and 2, angular position outputs generated by the encoder 83 specify the orientation of the scan sector with respect to the axis of rotation. Thus, those output signals can be used to determine the orientation of each scan plane. As illustrated in FIG. 2 sequential scan planes are generated and the relative 3-dimensional location of each reflective object in the organ under scrutiny can thus be specified by its 2-dimensional relationship within a B-scan obtained at a known scan plane orientation. This information can thus be used to determine 3-dimensional coordinates for a computer driven graphics display.

In FIG. 2, the angular increment $\Delta\theta$ between the scan planes is illustrated as the increment between scan planes 2 and 3. This can be controlled by signals from the angular position encoder 83, that is the output signals. For example data can be gated so that it is accepted only when $\theta$ is 5°. Additionally, control signals from the real-time B-scan scanner 77 may be used to determine when a new scan begins. Thus, using these options a single, complete scan can be displayed or acquired for digital analysis for each scan plane angular increment, i.e., 5° or the like. Additionally, as illustrated in FIG. 2, the area of the scan sector may itself be gated for purposes of digital data acquisition. The rf signals which are thus acquired from the real-time B-scan unit 77 and beam display module 79 are used as input to the computer analysis system. Such a system is described in "Theoretical Framework for Spectrum Analysis in Ultrasonic Tissue Characterization", Lizzi et al, J. Acoust. Soc. AM, Vol. 73, pp. 1366-73 (1983).

Figure 3:
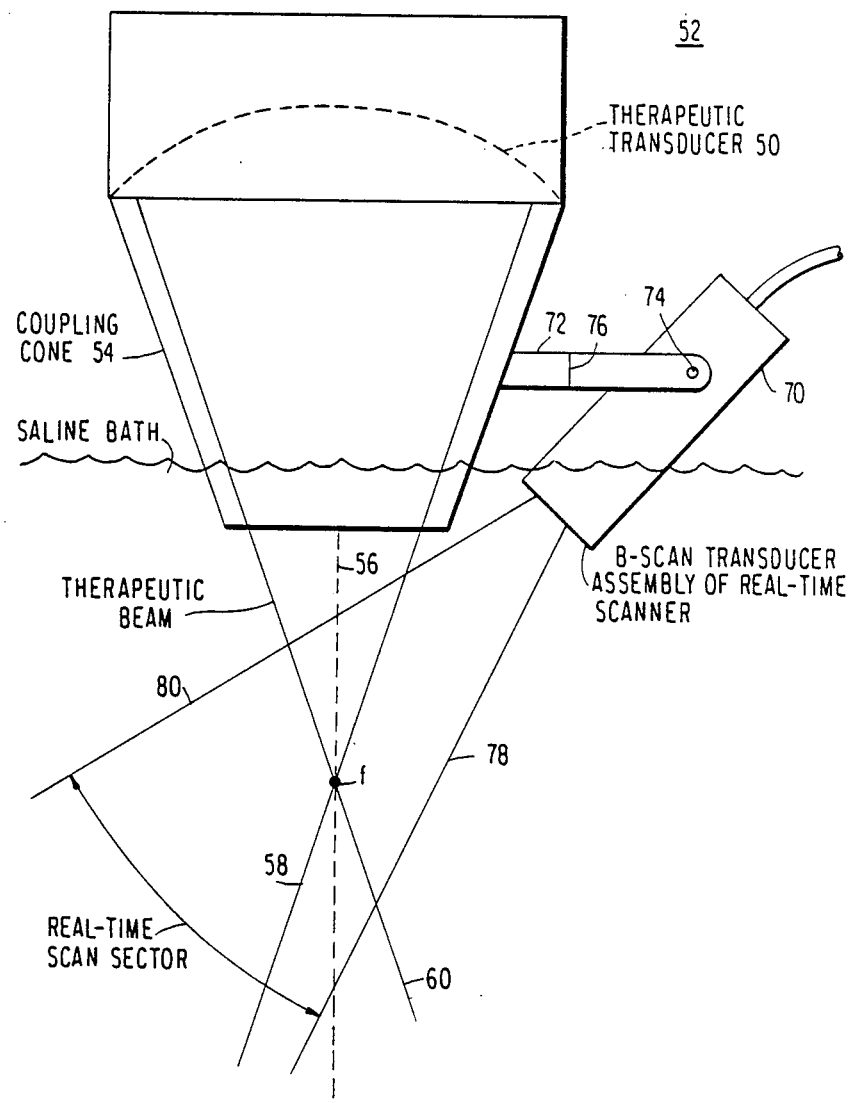
FIG. 3 is a schematic view of the real-time B-scan transducer and therapeutic transducer assembly for the presentation of cross sectional data.

FIG. 3 illustrates the side-looking coupling of the real-time B-scan unit with high-intensity focus therapeutic ultrasonic transducer. The therapeutic transducer assembly 52 comprises a high-intensity piezoelectric transducer 50 and a coupling cone 54 which is filled with degassed, distilled water held in place by a thin, acoustically transparent rubber membrane. (not shown). The specifics of the therapeutic transducer and its associated electronics are found in U.S. Pat. 4,484,569. The therapy beam produced by the therapeutic transducer 50 has a focal point (f) with the central axis of the therapy beam illustrated as dotted line 56. The edges of the therapy beam are defined by the lines 58, 60 converging to the focal point (f) and then diverging.

Figure 4:
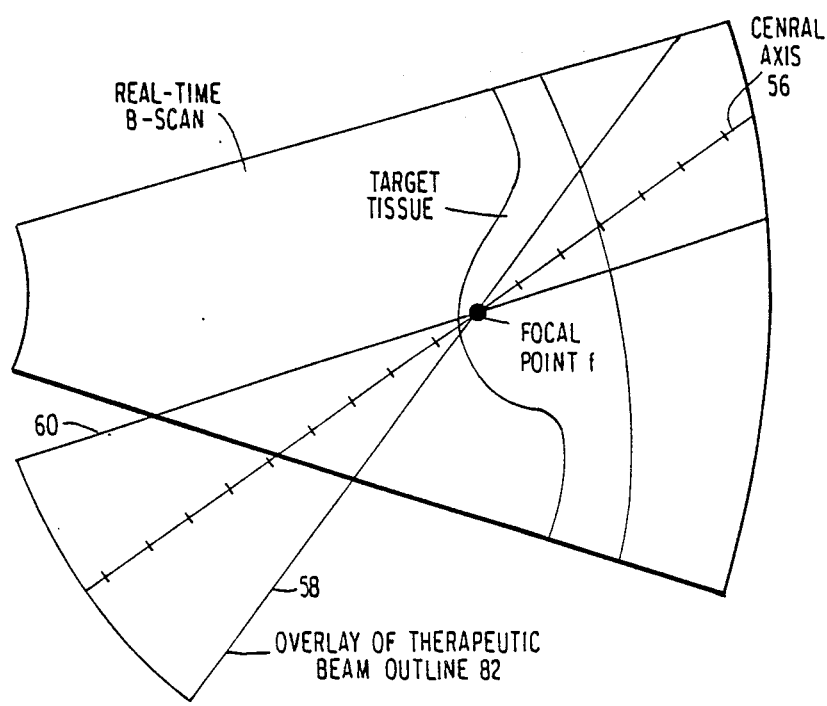
FIG. 4 is a diagram illustrating the display format of the therapeutic beam superimposed on the B-mode image.

Referring now to FIGS. 3 and 4, another aspect of this invention is depicted. In accordance with this aspect, the B-scan unit is employed for real-time aiming and monitoring. The diagnostic scanning transducer assembly 70 is a real-time 10MHz B-mode system coupled to the therapeutic transducer assembly 52 in a side-looking arrangement. Coupling of the diagnostic transducer assembly 70 to the therapeutic transducer assembly 52 is via the coupling 72. This coupling allows the transducer assembly 70 to pivot around point 74 and rotate at coupling point 76. The region covered by the diagnostic scanner beam is defined by lines 78, 80. As illustrated in FIG. 3, the real-time scan plane of the diagnostic transducer assembly 70 contains the central axis 56 of the therapeutic transducer. The attachment mount thus permits the practitioner to adjust the rotation, angulation, and position of the diagnostic transducer assembly 70. Once positioned, the transducer assembly 70 is locked into place.

One technique of achieving proper alignment of the diagnostic transducer assembly 70 is with a target comprising small, e.g. 1 mm diameter acoustically reflective spheres mounted on a straight wire. The target is aligned with the central axis 56 of the therapeutic transducer. The aiming light and the A-scan transducer associated with the therapeutic unit are focused on the top ball to adjust the vertical standoff distance. The therapeutic assembly is moved so that it's A-scan transducer (not shown) displays echoes from all of the spheres. That is, the axis of the beam is made coincident with the balls by adjusting the therapy transducer housing until all balls are centered in the light beam and generate A-scan echoes. The position and orientation of the B-scan transducer are then adjusted so that the chain of balls appears at maximum brightness in the B-scan display. Thus, the central axis 56 and the focal point (f) of the therapeutic transducer 50 is defined on the B-mode real-time display. In the B-scan display, the top ball specifies the location of therapy beam's focal point and the line of balls specifies the beam's axis. The separation between balls is known by measurement so that their B-scan echo locations can be used for proper spatial scaling of B-scan images. This information then is then used with beam calibration data to specify and position the beam overlay shown in FIG. 4. Beam calibration data can also comprise schlieren photographs and scans made with small piezoelectric probes. The diagnostic scanning transducer assembly is now aligned in a fixed relationship to the therapeutic focal point (f).

The scanning diagnostic transducer assembly 70 employs a mechanically scanned transducer that is rapidly scanned in a repetitive sector pattern that includes the path of the therapeutic transducer beam. This scanning obtains echoes from the tissue under evaluation which are displayed as cross-sectional images on the monitor of the real-time unit 77. Such a unit is the Coopervision Ultrasonic Digital-B System IV.

It is apparent that other scanning systems such as the piezoelectric arrays may be used.

Once the tranducer assembly 70 is aligned and locked in place, a plastic overlay 82, as illustrated in FIG. 4 which depicts the focal point (f) of the therapeutic beam, may be superimposed on the real-time B-scan display. FIG. 4 also illustrates the B-scan of the tissue in the real-time display.

Other information, instead of a simple beam outline, may be displayed in a manner illustrated in FIG. 4. This aids the physician to elect the best manner of treatment, i.e., heating a tumor while sparing adjacent tissues. Displays can be used to specify therapeutic beam intensity levels as a function of position. Tissue regions that may be altered by the beam can also be indicated; these regions can be specified by previous laboratory data (e.g., from animals) or theoretical analysis, see: Lizzi et al "Ultrasonic Hyperthermia for Opthalmic Therapy", IEEE Transaction on Sonics and Ultrasonics, SU-31(5) pp. 473-81 (1984). Expected temperature rises as function of position can also be depicted based on these sources of information. The above factors can be displayed as a function of system control settings that adjust the intensity or frequency of the therapy beam. All information for these displays is stored in the beam display module 79.

In operation, the practitioner aims the therapeutic transducer by moving the entire integrated assembly of therapeutic transducer 50 together with the scanning diagnostic transducer assembly 70 to scan tissue segments to be treated. Coupling to those tissue segments is attained by the saline bath, schematically illustrated in FIG. 3. Such scanning also depicts the central axis 56 and boundaries 58, 60 of the therapeutic beam. This is illustrated in FIG. 4. The practitioner can thus assess which tissues lie within the therapeutic beam and reorient the transducer so that the therapeutic beam is focussed at the desired point such that other non-target tissues lie outside the therapeutic beam or in regions of low-intensity. By rotating the scanning transducer assembly, he can perform these adjustments with thorough 3-dimensional information on both tissue geometry and on the geometry of the therapeutic beam. The tissue to be treated then properly placed within the target zone of the therapeutic beam, is exposed to high-intensity ultrasound with real-time B-scans used to assess desired and undesired tissue changes in 3-dimensions.

Such a system represents a material advantage over prior systems which do not permit a thorough real-time, 3-dimensional assessment of tissue positions and responses relative to the placement of the therapeutic beam. Current systems prior to this invention do not permit the complete observation of the size and shape of therapeutic lesions nor do they present a complete representation of tissue motion. An example of such tissue motion is in vitreous hemorrhage exposed to high intensity ultrasound. By monitoring the insonified tissue during and immediately after insonification, dynamic responses within tissue can be documented.

The system in accordance with this invention finds utilization in many types of treatment including slow heating where the defocussed part of the therapy beam is employed. It is also used for rapid ablation utilizing the focal point. The system also finds utility in producing a spatial matrix of lesions to completely treat a tumor.

Specific examples of the applications of this system will now be provided.

For clinical hyperthermia treatments of ocular tumors, this invention has found particular utilization in the B-mode imaging to position the tumor in the diverging portion of the therapeutic beam. This assures that the therapeutic focal point is situated in the vitreous humor where it produces no significant effect. (see Coleman, D. J. et al. "Ultrasonic Hyperthermia and Radiation in the Management of Intraocular Malignant Melanoma", Amer. Jo. Ophthal., 101:635, 1986). The tumor is then exposed to moderate intensities in the order of $1W/cm^2$ for 15 minutes to achieve a temperature near 43° C. Because, in this treatment the therapeutic exposure tends to interfere with the B-mode display given electronic and acoustic pick-up, the therapeutic excitation signal is blanked at 5 second intervals to periodically monitor beam positioning. This interference can be overcome by filtering techniques.

This invention has also been employed for experiments to observe lesion placement relative to the focal point of the therapeutic beam and to study the dynamics of lesion formation and tissue motion. Lesion formation was studied in nude athymic mice having human tumor transplants. In this application, high-intensity exposures are delivered utilizing positioning as illustrated in FIGS. 3-4. Utilizing B-mode images, it is possible to rapidly and accurately place lesions in a contiguous fashion intended to treat the entire tumor. Such cannot be quickly accomplished in prior systems that do not permit complete real-time analysis of tissue as treatment proceeds. Complete 3-dimensional treatment with contiguous lesions can be accomplished using the 3-dimensional scanning discussed herein.

Figure 5A:
FIG. 5A and FIG. 5B are B-scan images of a liver sample before and after ultrasonic exposure in a lesion placement experiment.
Figure 5B:
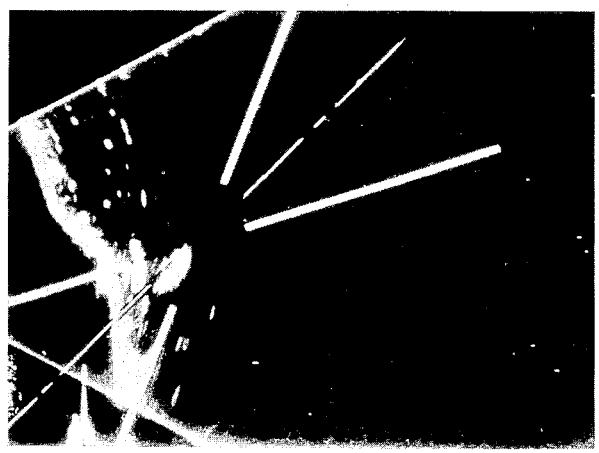

This invention is also applicable to in-vitro experimentation on liver samples where lesion positioning and size can be more extensively studied. Reference is made to FIG. 5A wherein a B-mode image of a 2.5-3.0 cm section of a liver is illustrated pre-exposure. FIG. 5B is a B-mode image of the liver section following a 1 second exposure. The therapeutic focal point was 20 mm below the surface. In this experiment, the 2.5-3.0 cm liver sample is place placed in a saline-tank resting on an absorbing sponge material. This prevents standing wave formation from the bottom of the tank. Since the beam overlay does not photograph well, FIGS. 5A and 5B have corresponding lines superimposed on the photographs.

FIG. 5B illustrates the same liver sample immediately following a 1.0 second exposure to 4.65 MHz pulse having a spatial average intensity exceeding $5KW/cm^2$. As illustrated in FIG. 5B, the lesion is visualized and has a maximum dimension of approximately 3 mm. The lesion in FIG. 5B has an ellipsoidal shape with a center located in front of the focal point.

Figure 6A:
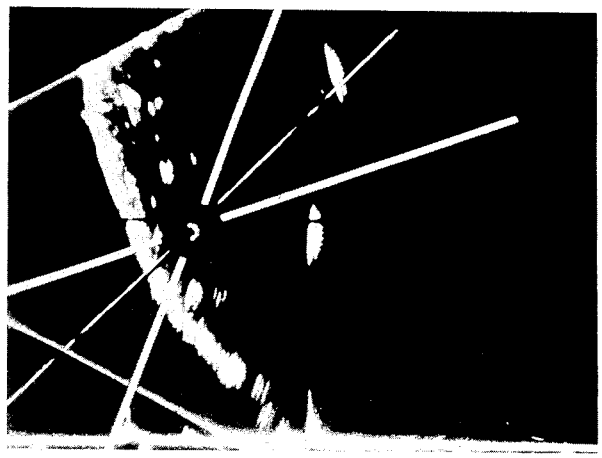
FIG. 6A and FIG. 6B are B-scan images of a liver sample before and after ultrasonic exposure in a second lesion placement experiment.
Figure 6B:
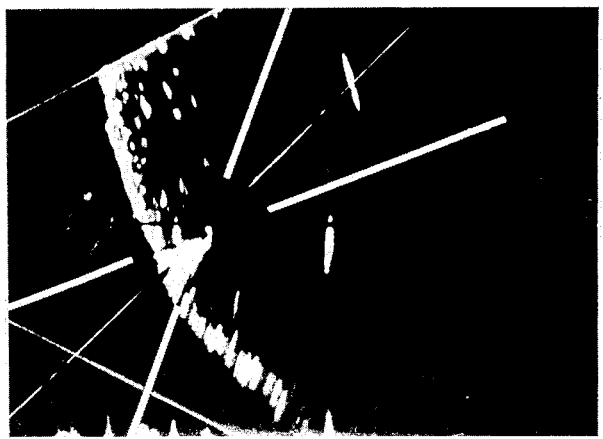

FIGS. 6A and 6B illustrate pre- and post-exposure images using the same acoustic parameters but with the therapeutic focal point placed closer to the surface of the liver. Here, as illustrated, a wedge-shaped lesion is formed in close conformity to the geometric outline of the therapeutic beam. Again, lines are superimposed on photographs. The anterior placement of the lesion with respect to the focal point is illustrated in FIG. 6B.

In this experiment, the therapeutic focal point was placed 15 mm below the surface.

The fidelity of the lesion images was checked by dissecting exposed liver samples and measuring the lesions with a caliper. The lesions were observed as discolored regions with visible vacuoles. The dimensions of the lesions were found to be in excellent agreement with measurements obtained from the corresponding real-time B-mode images. The anterior placement of lesions produced at high intensities has been observed in both liver and in nude athymic mice tumors.

While it is appreciated that FIGS. 5 and 6 represent applications of B-mode visualization in pre and post exposures, this invention finds important utilization in the dynamic observation performed during pulse exposures of the therapeutic beam and following continuous wave exposures.

It has been observed in high-intensity exposure of liver samples using 0.2 second pulses at 1 Hz pulse repetition rates, that the first several pulses will elicit slight transient effects, presumably due to heating and cooling of tissue with concomitant changes in local values of acoustic impedance. Lesions that are large compared to the beam width can form suddenly after, for example, the third or fourth acoustic pulse. Such is observed in real-time. The sudden appearance of these lesions is consistent with a lesion threshold while the relatively large size is deemed to be due to thermal conduction which broadens the area of temperature elevation during preceding pulses.

Another example of dynamic observation is in fresh blood injected in-vitro rabbit eyes for purposes of simulating recent hemorrhaging. Real-time motion was detected following high-intensity pulses. If the intensity is sufficiently high, ejection of blood was observed from the injected mass rapidly emerging into the gel-like vitreous humor. Small surface and internal movements were observed after high-intensity pulses as short as 5 milliseconds.

While this invention has been described relative to its preferred embodiment with examples of 3-dimensional and real-time diagnostic and therapeutic applications, it is apparent that modifications of the system fall within the scope of the invention. For example, while mechanical scanning to obtain serial planes is portrayed, a 2-dimensional array transducer can be employed. Such an array scans electronically by controlling the excitation pulses to each array element. The array would be housed in the transducer assembly 70 but fixed in place. The elements of the array would be electrically scanned in 2-dimensions by timed excitation pulses. Since the array is fixed in a known relationship, scan lines with a known orientation can be generated. Such a system offers important advantages in terms of compactness and speed.

Additionally, injected electrical signals may be used to replace the overlays illustrated in FIG. 4 to depict the therapy beam. Consequently, in each of the above scan planes, one could depict the corresponding perimeter of the therapy beam.

Another modification would be the use of several diagnostic transducers. Because of electrical and acoustic pick-up, some applications, the diagnostic transducer may not be employed in some instances when the therapy beam is on. This deficiency could be solved by using a therapy frequency outside the range of the diagnostic system or by filtering techniques to reject the narrow-band components of the therapy transducer.

Also, the orientation of the scanning transducer can be moved to be placed in the center of the therapy transducer. In this orientation, for example, in the position where the A-scan transducer 51 is illustrated in FIG. 1, 3-dimensional scanning may still take place.

Other scan plane movement patterns are also possible. For example rotating the real time transducer assembly 70 about its central axis with appropriate position encoders can also supply 3-dimensional information.

Another location would be mounting on a ring encircling the therapeutic transducer housing cone 54. This would permit re-positioning of the scanning transducer.

The availabilty of obtaining 3-dimensional data also allows for important systems changes to be made resulting in new techniques of performing various procedures. For example, by using a feedback path from the real-time B-scan unit 77 through the computer tissue analysis system 57 to the therapeutic excitation unit 53, real-time control of the excitation energy can be achieved. The computer would, in real-time analyze B-scan data and compare to established parameters to control the energy level of the therapeutic excitation unit. One example would be a significant shift in B-scan image data indicating that the patient has moved. In this case, the unit would be shut-off.

In another example, the input energy could be modified based on B-scan grey scale features of a lesion. Such features can include the size, shape or brightness of the lesion in the B-scan display. In the case of vitreous hemorrhage the energy levels would be modified based on hemorrhage movement caused by the therapeutic beam so that high energy would be used only when the target is aligned in the focal zone of the therapeutic transducer. Using this feedback technique, a pattern of excitation energy could follow a therapeutic curve based on the analysis in real-time of tissue change.

In that regard, since data is obtained from different scan planes to provide 3-dimensional data, volume computations of tumors and lesions may be made by simple mathematical analysis of the integrated 2-dimensional data received from each scan plane. This is an important advantage available because 3-dimensional data is obtained by the system.

This system also allows the accurate, simultaneous aiming of multiple therapeutic transducers on desired tissues. Current ophalphomic systems use only a single transducer which is repositioned between applications of ultrasound. In accordance with this invention, it is now possible to use a group of therapeutic transducers, either fixed or movable. This provides for different aiming points on the target as well as the advantage of realigning one transducer while another is in use. Consequently, simultaneous treatment and positioning is therefore accomplished which shortens the length of the procedure. as can be appreciated, such requires 3-dimensional data.

The use of 3-dimensional data as defined in this description is not limited to ultrasound treatment procedures. Such finds ready application in therapeutic laser and microwave procedures, in biopsies, in radiotherapy and for example procedures such as amniocentesis.

Having described our invention, we claim:

1. A system for obtaining 3-dimensional ultrasonic images of an object under study comprising:
an ultrasonic transducer assembly, said transducer assembly producing ultrasonic pulses directed toward said object and producing 2-dimensional data from a radio frequency output in response to ultrasonic echo pulses received,
means to generate 2-dimensional data in sequential scan planes separated from each other by an angular increment,
means to determine the angular increment between said sequential scan planes and produce output position signals and,
signal processing means receiving said 2-dimensional data from said ultrasonic transducer assembly and the output position signals from said means to determine the angular increment and generating 3-dimensional cross-sectional data of said object,
wherein said means to generate sequential scan planes comprises a handle coupled to said transducer assembly, said handle manually movable to rotate said ultrasonic transducer assembly about an axis perpendicular to said scan plane.

2. The system of claim 1 wherein said means to generate sequential scan planes comprises an electrical motor coupled to said transducer assembly to rotate said ultrasonic transducer assembly about an axis perpendicular to said scan plane.

3. The system of claim 2 wherein said motor is a stepper motor.

4. The system of claim 3 wherein said means to determine the angular increment comprises means to provide a predetermined input voltage to said stepper motor wherein said predetermined input voltage causes a known rotation of said motor to produce a known angular rotation in said transducer assembly.

5. The system of claim 4 wherein said means to generate sequential scan planes comprises a handle coupled to said transducer assembly and manually moved to rotate said ultrasonic transducer assembly about an axis perpendicular to said scan plane.

6. The system of claim 1 wherein said means to determine the angular position comprises an optical encoder mounted to said transducer to sense rotation thereof and generate said output position signals.

7. The system of claim 1 wherein said means to determine the angular position comprises a position encoding potentiometer.

8. The system of claim 1 wherein said transducer comprises piezoelectric array and said means to generate sequential scan planes of ultrasonic echo pulses comprises means for controlling excitation pulses to each element in said array.

9. The system of claim 8 wherein said means to determine the angular increment between said sequential scan planes comprises control means to determine the order of excitation pulses to each element in said array.

10. The system of claim 1 further comprising a therapeutic transducer assembly coupled to said ultrasonic transducer assembly, said therapeutic transducer including means producing a high energy ultasonic beam focused to converge at a focal point and wherein said scan planes of said ultrasonic transducer overlap said high energy ultasonic beam and said focal point.

11. The system of claim 10 further comprising means to excite said therapeutic transducer assembly.

12. The system of claim 1 wherein said ultrasonic transducer assembly comprises a piezoelectric transducer, and further comprising a real-time B-scan module to excite said piezoelectric transducer and to process said radio frequency output signals and a beam display module to produce a B-scan output.

13. The system of claim 12 further comprising computer means to receive the B-scan output for analysis of the object.

14. The system of claim 12 further comprising display means receiving said B-scan output from one of said scan planes in real-time, said display means having an overlay representing positioning data.

15. The system of claim 14 wherein said overlay contains an outline of a therapeutic beam and its focal point.

16. The system of claim 12 further comprising means to rotate said piezoelectric transducer about an axis perpendicular to a scan plane, whereby a scan sector in said scan plane is shifted.

17. The system of claim 1 further comprising a therapeutic transducer, means defining a feedback path from said signal processing means to said therapeutic transducer to vary the output thereof in real-time based on analysis of tissue by said signal processing means.

18. The system of claim 17 wherein said ultrasonic transducer is a B-scan device and said signal processing means receives said radio frequency output of said B-scan device for tissue analysis based on predetermined operational parameters.

19. The system of claim 1 further comprising a plurality of therapeutic transducers positioned at spaced locations, means to move any one of said plurality of therapeutic transducers to a new position while another of said plurality of therapeutic transducers is excited to produce a therapeutic beam.

20. The system of claim 1 further comprising means to determine the volume of said object based on said 3-dimensional cross-sectional data.

21. A system for obtaining 3-dimensional ultrasonic images of an object under study comprising:
an ultrasonic transducer assembly, said transducer assembly producing ultrasonic pulses directed toward said object and producing 2-dimensional data from a radio frequency output in response to ultrasonic echo pulses received,
means to generate 2-dimensional data in sequential scan planes separated from each other by an angular increment,
position encoding potentiometer means to determine the angular increment between said sequential scan planes and produce output position signals and,
signal processing means receiving said 2-dimensional data from said ultrasonic transducer assembly and the output position signals from said means to determine the angular increment and generating 3-dimensional cross-sectional data of said object.

22. A system for obtaining 3-dimensional ultrasonic images of an object under study comprising:
an ultrasonic transducer assembly, said transducer assembly producing ultrasonic pulses directed toward said object and producing 2-dimensional data from a radio frequency output in response to ultrasonic echo pulses received,
means to generate 2-dimensional data in sequential scan planes separated from each other by an angular increment,
means to determine the angular increment between said sequential scan planes and produce output position signals, signal processing means receiving said 2-dimensional data from said ultrasonic transducer assembly and the output position signal from said means to determine the angular increment and generating 3-dimensional cross-sectional data of said object, a plurality of therapeutic transducers positioned at spaced locations, and means to move any one of said plurality of therapeutic transducers to a new position while another of said plurality of therapeutic transducers is excited to produce a therapeutic beam.

23. A system for obtaining 3-dimensional ultrasonic images of an object under study comprising:
a piezoelectric ultrasonic transducer assembly, said transducer assembly producing ultrasonic pulses directed toward said object and producing 2-dimensional data from a radio frequency output in response to ultrasonic echo pulses received,
means to generate 2-dimensional data in sequential scan planes separated from each other by an angular increment,
means to determine the angular increment between said sequential scan planes and produce output position signals,
signal processing means receiving said 2-dimensional data from said ultrasonic transducer assembly and the output position signals from said means to determine the angular increment and generating 3-dimensional cross-sectional data of said object,
a real-time B-scan module to excite said piezoelectric transducer and to process said radio frequency output signals,
a beam display module to produce a B-scan output, and
display means receiving said B-scan output from one of said scan planes in real-time, said display means having an overlay representing positioning data.

24. A system for obtaining 3-dimensional ultrasonic images of an object under study comprising:
a rotatable ultrasonic transducer assembly, said transducer assembly producing ultrasonic pulses directed toward said object and producing 2-dimensional data from a radio frequency output in response to ultrasonic echo pulses received,
means to generate 2-dimensional data in sequential scan planes separated from each other by an angular increment,
optical encoder means mounted to said transducer assembly to determine the angular increment between said sequential scan planes and produce output position signals by sensing rotation of said assembly and,
signal processing means receiving said 2-dimensional data from said ultrasonic transducer assembly and the output position signals from said means to determine the angular increment and generating 3-dimensional cross-sectional data of said object.

25. The system of claim 24, wherein said means to generate sequential scan planes comprises a handle coupled to said transducer assembly which is manually movable to rotate said ultrasonic transducer assembly about an axis perpendicular to said scan plane.

26. The system of claim 23 further comprising a plurality of ultrasonic transducers for diagnostic application.

27. The system of claim 22 wherein said means to determine the angular position comprises an optical encoder mounted to said transducer to sense rotation thereof and generate said output position signals.

28. The system of claim 22 wherein said means to determine the angular position comprises a position encoding potentiometer.

29. The system of claim 21 wherein said means to generate sequential scan planes comprises an electrical motor coupled to said transducer assembly to rotate said ultrasonic transducer assembly about an axis perpendicular to said scan plane.

30. The system of claim 29 wherein said motor is a stepper motor.

31. The system of claim 30 wherein said means to determine the angular increment comprises means to provide a predetermined input voltage to said stepper motor wherein said predetermined input voltage causes a known rotation of said motor to produce a known angular rotation in said transducer assembly.

32. The system of claim 21 wherein said transducer comprises piezoelectric array and said means to generate sequential scan planes of ultrasonic echo pulses comprises means for controlling excitation pulses to each element in said array.

33. The system of claim 32 wherein said means to determine the angular increment between said sequential scan planes comprises control means to determine the order of excitation pulses to each element in said array.

34. The system of claim 21 further comprising a therapeutic transducer assembly coupled to said ultrasonic transducer assembly, said therapeutic transducer including means producing a high energy ultrasonic beam focused to converge at a focal point and wherein said scan planes of said ultrasonic transducer overlap said high energy ultrasonic beam and said focal point.

35. The system of claim 34 further comprising means to excite said therapeutic transducer assembly.

36. The system of claim 21 wherein said ultrasonic transducer assembly comprises a piezoelectric transducer, and further comprising a real-time B-scan module to excite said piezoelectric transducer and to process said radio frequency output signals and a beam display module to produce a B-scan output.

37. The system of claim 36 further comprising computer means to receive the B-scan output for analysis of the object.

38. The system of claim 36 further comprising display means receiving said B-scan output from one of said scan planes in real-time, said display means having an overlay representing positioning data.

39. The system of claim 38 wherein said overlay contains an outline of a therapeutic beam and its focal point.

40. The system of claim 36 further comprising means to rotate said piezoelectric transducer about an axis perpendicular to a scan plane, whereby a scan sector in said scan plane is shifted.

41. The system of claim 21 further comprising a therapeutic transducer, means defining a feedback path from said signal processing means to said therapeutic transducer to vary the output thereof in real-time based on tissue analysis of said signal processing means.

42. The system of claim 41 wherein said ultrasonic transducer is a B-scan device and said signal processing means receives said radio frequency output of said B-scan device for tissue analysis based on predetermined operational parameters.

43. The system of claim 21 further comprising a plurality of therapeutic transducers positioned at spaced locations, means to move any one of said plurality of therapeutic transducers to a new position while another of said plurality of therapeutic transducers is excited to produce a therapeutic beam.

44. The system of claim 21 further comprising means to determine the volume of said object based on said 3-dimensional cross-sectional data.

* * * * *